(12) United States Patent
Niklason et al.

(10) Patent No.: US 6,443,156 B1
(45) Date of Patent: Sep. 3, 2002

(54) SEPARABLE DOUBLE LUMEN ENDOTRACHEAL TUBE

(76) Inventors: Laura E. Niklason, 3301 Carriage Trail, Hillsborough, NC (US) 27278; Loren T. Niklason, 3301 Carriage Trail, Hillsborough, NC (US) 27278

( * ) Notice: Subject to any disclaimer, the term of this patent is extended or adjusted under 35 U.S.C. 154(b) by 113 days.

(21) Appl. No.: 09/630,751

(22) Filed: Aug. 2, 2000

(51) Int. Cl.⁷ .............................................. A61M 16/00
(52) U.S. Cl. ................................................. 128/207.14
(58) Field of Search ....................... 128/200.24, 200.26, 128/201.24, 202.27, 204.18, 207.14, 207.15, 207.18, 911, 912; 604/94.01

(56) References Cited

U.S. PATENT DOCUMENTS

| | | | |
|---|---|---|---|
| 4,233,984 A | * 11/1980 | Walling .................. | 128/207.14 |
| 4,674,495 A | * 6/1987 | Orr ........................ | 128/207.14 |
| 4,840,172 A | * 6/1989 | Augustine et al. ..... | 128/207.14 |
| 4,875,165 A | 10/1989 | Fencil et al. | |
| 5,065,755 A | * 11/1991 | Klafta .................... | 128/200.26 |
| 5,067,497 A | * 11/1991 | Greear et al. .......... | 128/207.14 |
| 5,241,956 A | * 9/1993 | Brain ..................... | 128/207.14 |
| 5,253,643 A | * 10/1993 | Price ..................... | 128/207.14 |
| 5,315,992 A | * 5/1994 | Dalton .................. | 128/207.14 |
| 5,318,517 A | * 6/1994 | Reiman ................. | 128/207.14 |
| 5,372,131 A | * 12/1994 | Heinen, Jr. ............ | 128/200.26 |
| 5,506,877 A | 4/1996 | Niklason et al. | |
| 5,588,424 A | * 12/1996 | Insler et al. ........... | 128/200.24 |
| 5,709,691 A | * 1/1998 | Morejon ................ | 128/207.14 |
| 5,765,559 A | 6/1998 | Kim | |
| 5,791,338 A | 8/1998 | Merchant et al. | |
| 5,803,078 A | * 9/1998 | Brauner ................. | 128/200.14 |
| 5,803,079 A | 9/1998 | Rogers et al. | |
| 5,865,176 A | * 2/1999 | O'Neil ................... | 128/207.14 |
| 5,872,828 A | 2/1999 | Niklason et al. | |
| 5,873,362 A | 2/1999 | Parker | |
| 5,894,840 A | 4/1999 | King | |
| 5,941,246 A | 8/1999 | Roopchand | |
| 5,957,134 A | * 9/1999 | Lee ........................ | 128/207.14 |

* cited by examiner

Primary Examiner—John G. Weiss
Assistant Examiner—Teena Mitchell
(74) Attorney, Agent, or Firm—Jenkins & Wilson, P.A.

(57) ABSTRACT

A separable double lumen endotracheal tube is disclosed having a first lumen and a second lumen and which are removably affixed together to allow the first lumen to be separated from the second lumen of the double lumen endotracheal tube and, if desired, to be subsequently affixed together again. Either lumen of the double lumen endotracheal tube can function alone for positive pressure ventilation, but normally the bronchial lumen will be removed from a patient and the tracheal lumen left in place to function alone to provide positive pressure ventilation as required by a patient. The double lumen endotracheal tube will, however, function to allow the bronchial lumen to remain in a patient subsequent to removal of the tracheal lumen as a matter of choice during a medical procedure.

18 Claims, 12 Drawing Sheets

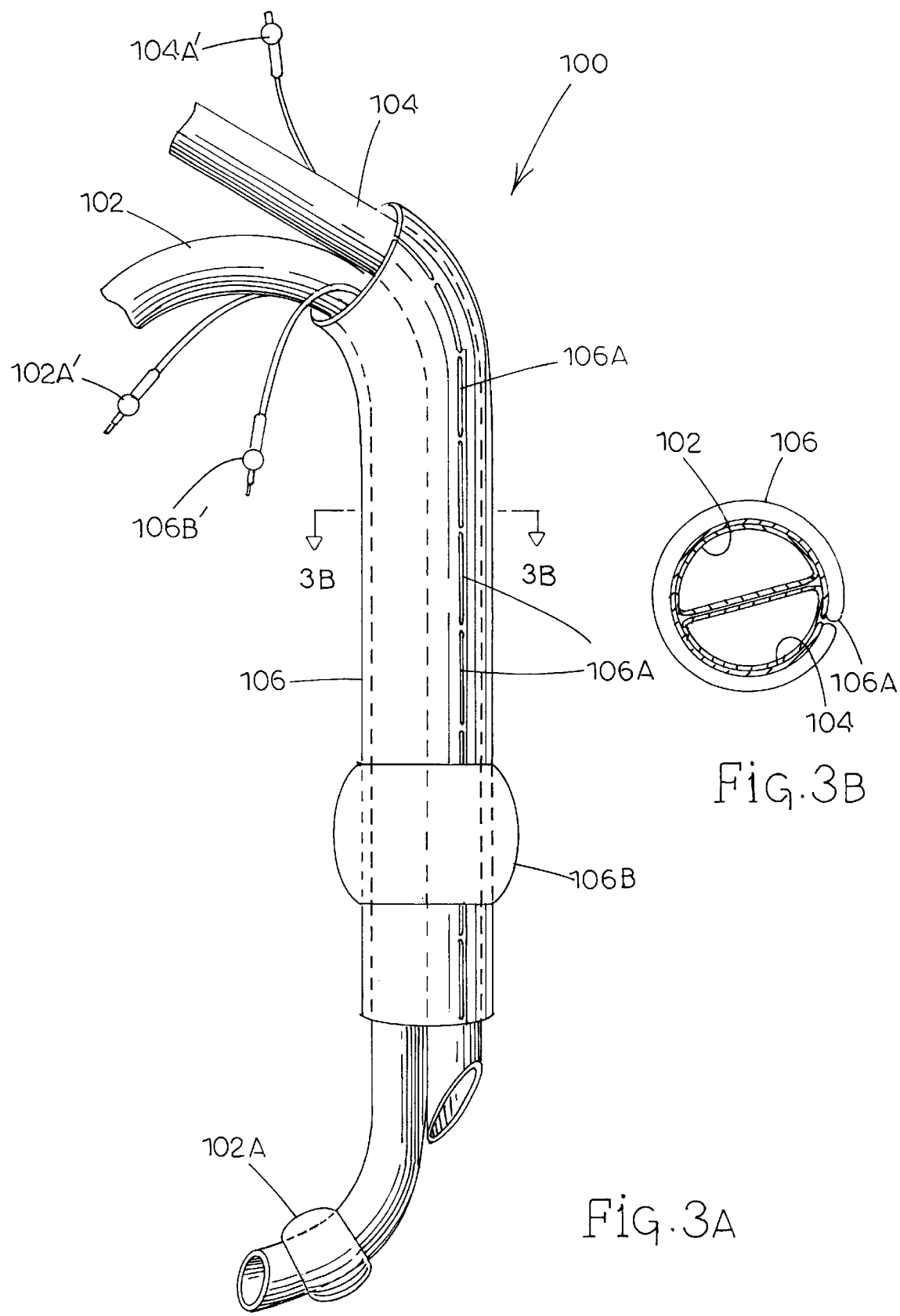

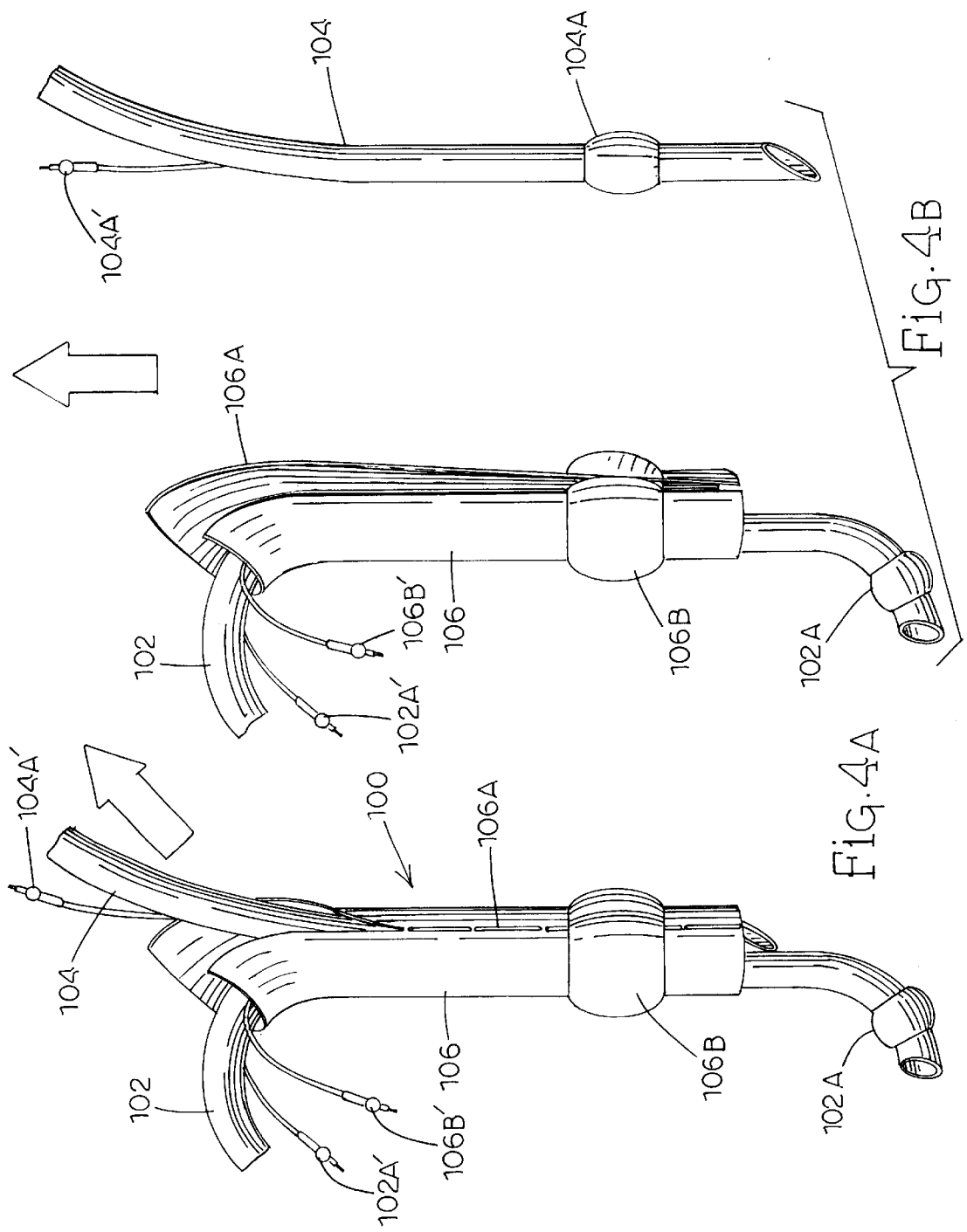

SEPARABLE DOUBLE LUMEN ENDOTRACHEAL TUBE

FIELD OF THE INVENTION

The present invention relates to endotracheal tubes for ventilation of the lungs, and more particularly to an improved double lumen endotracheal tube that allows for inserting both bronchial and tracheal lumens together and then separating and removing the bronchial lumen to allow for continued tracheal, ventilation.

RELATED ART

Endotracheal tubes are used to couple a patient's respiratory system to a breathing apparatus during surgical procedures or emergency situations. A typical endotracheal tube is made of PVA (polyvinyl chloride) or similar material and has an inflatable cuff positioned several centimeters from an end of the tube that is inserted into the trachea. Thus, the tube can be sealed relative to the trachea by inflating the cuff through an inflation line extending along the endotracheal tube. A fitting on an opposite end of the tube couples the endotracheal tube to an artificial respirator or ventilator. This type of device is well known to those skilled in the medical arts.

As is also well known to those skilled in the medical arts, a double lumen endotracheal tube is required in many kinds of lung or major vascular surgery when it is necessary to ventilate both the left and right lungs separately. A conventional double lumen endotracheal tube provides for individualized ventilation of the two lungs with two lumens each having a cuff positioned therearound. The bronchial lumen may extend into either the right or left mainstem bronchus while the tracheal lumen remains in the trachea. The usefulness of this conventional-type of double lumen endotracheal tube is limited by its large diameter which can unfortunately lead to bronchial damage and even vocal chord scarring when it is left in place for a long post-operative period. Thus, when post-operative ventilatory support is anticipated for a patient, the double lumen endotracheal tube is usually removed at the end of the operation and is replaced with a conventional single lumen tube. However, the conventional double lumen endotracheal tube can be associated with significant upper airway swelling due to massive fluid resuscitation during the course of a surgical operation. Under these circumstances, replacement of the double lumen endotracheal tube with a single lumen tube in order to attempt to minimize the aforementioned bronchial damage and vocal chord scarring can be a potentially hazardous and occasionally life-threatening procedure. This is due to the fact that it can be very difficult for an anesthesiologist to see the upper airway and vocal chords adequately to replace the single lumen tube in the swollen upper airway. If it does prove difficult for the anesthesiologist to replace the double lumen endotracheal tube with the single lumen tube, a patient may be threatened with hypoxia and asphyxiation, and death.

These shortcomings are overcome by the separable double lumen endotracheal tube of the present invention which meets a long-felt need for a double lumen endotracheal tube that poses less risk to a patient when upper airway swelling has occurred during the course of a surgical operation.

SUMMARY OF THE INVENTION

In accordance with the present invention, a separable double lumen endotracheal tube is provided comprising a first tubular member defining a first lumen therethrough. A separately formed second tubular member is provided that defines a second lumen therethrough and which is removably affixed to the first tubular lumen. Thus, the first tubular member can be removed from the airway of a patient while allowing the second tubular member to remain in a patient's airway.

Also, a method is provided for intubating a patient with a double lumen endotracheal tube comprising the steps of providing a separable double lumen endotracheal tube comprising a first tubular member defining a first lumen therethrough and a second removably affixed tubular member defining a second lumen therethrough. The patient is then intubated with the double lumen endotracheal tube such that the first tubular member serves as a bronchial tube and the second tubular member serves as a tracheal tube. Next, the first tubular member is removed from a patient by separating and withdrawing the first tubular member from a patient such that the second tubular member remains in position in an intubated patient's trachea.

Accordingly it is an object of the present invention to provide a double lumen endotracheal tube which allows for separation and removal of one lumen from a patient while allowing the other lumen to remain in place in an intubated patient.

It is another object of the present invention to provide a method for intubating a patient with a double lumen endotracheal tube that allows for removal of the bronchial lumen when post-operative ventilatory support is anticipated while leaving the tracheal lumen in place in the trachea of a patient.

It is another object of the present invention to provide a double lumen endotracheal tube which allows for tracheal intubation, followed by bronchial intubation, which is then followed by brochial extubation.

It is still another object of the present invention to provide a double lumen endotracheal tube which allows for intubating a patient with the tracheal lumen and then slidably attaching and inserting the bronchial lumen into place later in a patient, and then selectively sliding and removing the bronchial lumen from a patient.

It is still another object of the present invention to provide a double lumen endotracheal tube which includes a bronchial lumen and a tracheal lumen which are removably affixed and which double lumen endotracheal tube allows for positive pressure ventilation of each individual lung when both lumens are attached or of both lungs together when only the tracheal lumen is in place in a patient.

Some of the objects of the invention having been stated hereinabove, other objects will become evident as the description proceeds, when taken in connection with the accompanying drawings as best described hereinbelow.

BRIEF DESCRIPTION OF THE DRAWINGS

FIG. 3A is a pictorial diagram of one embodiment of the separable double lumen endotracheal tube of the present invention depicting the sheath surrounding both lumens;

FIG. 3B is a cross-sectional view taken in a direction of arrows 3B—3B in FIG. 3A;

FIG. 4A is a pictorial diagram of the separable double lumen endotracheal tube of the invention wherein the first lumen and sheath are initially being separated from the second lumen;

FIG. 4B is a pictorial diagram of the separable double lumen endotracheal tube of the present invention wherein the first lumen and sheath have been separated and removed from the second lumen in a manner described in detail hereinafter;

DETAILED DESCRIPTION OF THE INVENTION

Figure 1A:
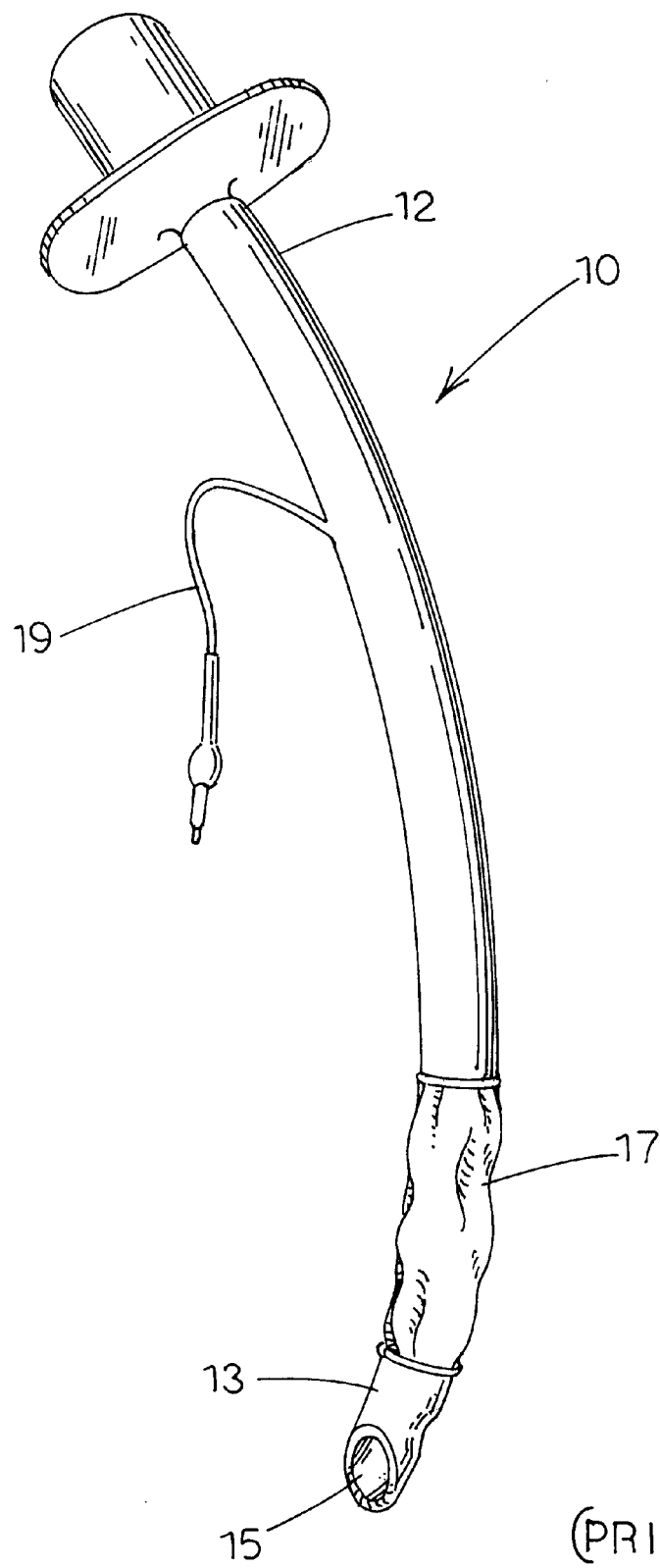
FIG. 1A is a pictorial diagram of a conventional endotracheal tube outside the patient with the cuff deflated.
Figure 1B:
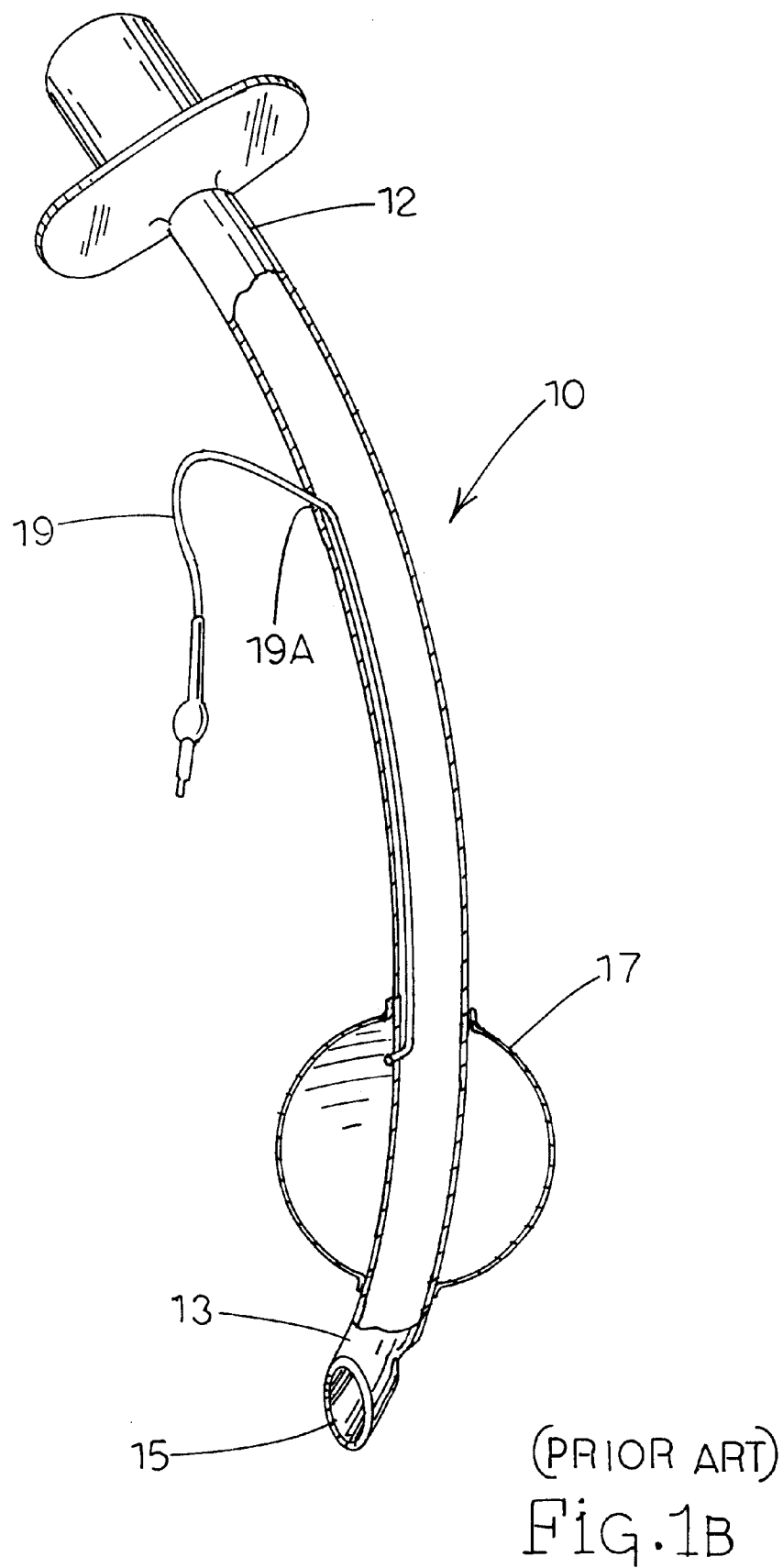
FIG. 1B is a pictorial diagram of a conventional endotracheal tube outside the patient with the cuff inflated.

Referring now to the drawings, a conventional single lumen endotracheal tube is shown in FIGS. 1A and 1B of the drawings and generally designated 10. Endotracheal tube 10 comprises a proximal end 12 and a distal end 13. The proximal end 12 is terminated in a connector that is adapted for connection to a regulated breathable air supply pump for introduction of gasses into a patient's lungs in order to maintain positive pressure in the lungs and thereby assist the patient to breathe during a medical procedure being administered during endotracheal intubation. Prior art endotracheal tube 10 extends from the patient's mouth and into the trachea in the form of a cannula having an open longitudinally-extended interior known to one skilled in the art as the lumen. The cannula or lumen is open at the distal end 13 so as to form distal opening 15. Distal opening 15 is typically formed at an acute angle to the longitudinal axis of the cannula formed by endotracheal tube 10 so as to provide a larger open area and to allow creation of a soft rounded edge to distal opening 15 of the lumen. The larger area of distal opening 15 of the lumen of endotracheal tube 10 serves to avoid obstruction of the lumen while the rounded edges serve to avoid tearing of the tissue by which the cannula of endotracheal tube 10 passes upon insertion into the throat of a patient. The narrow pointed distal opening 15 of single lumen endotracheal tube 10 also allows the cannula to work its way through portions of a patient's larynx, pharynx, and trachea that sometimes are partially closed off. Conventional single lumen endotracheal tube 10 is normally constructed of a radio-opaque bio-compatible PVA (polyvinyl chloride) tubing to provide resilience and flexibility to endotracheal tube 10.

Figure 1C:
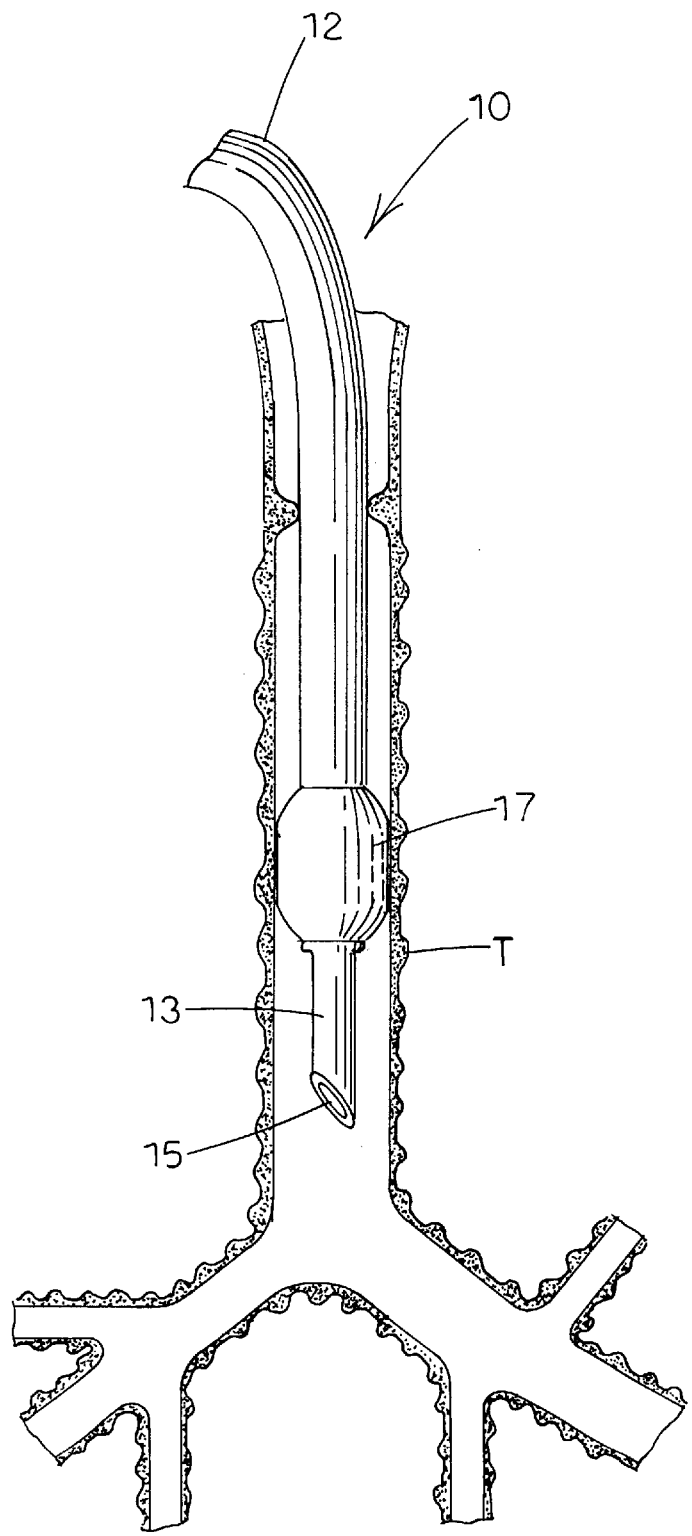
FIG. 1C is a pictorial diagram of a conventional endotracheal tube inside a patient's trachea with the cuff inflated.

Further shown in FIG. 1A and FIG. 1B is inflatable cuff 17 provided round the cannula of the single lumen endotracheal tube 10 proximate to distal end 15. FIG. 1A shows inflatable cuff 17 deflated and FIG. 1B shows inflatable cuff 17 in its inflated mode. Cuff 17 is also typically constructed of biocompatible PVA (polyvinyl chloride) but with a thin wall so as to facilitate inflation and deflation of the cuff. When inflatable cuff 17 is inflated, the cuff 17 will adapt to the natural shape of the trachea T (see FIG. 1C) while providing the required seal by contact with a minimal area of the tracheal wall. Inflatable cuff 17 of single lumen endotracheal tube 10 is inflated and deflated through a cuff inflation line 19 which extends from cuff 17 to the proximal end 12 outside of the patient's mouth (see FIG. 1B). Cuff inflation line 19 is connected to cuff 17 using conventional construction techniques well known in the endotracheal tube art; and cuff inflation line 19 is bonded to the inside wall of the cannula of endotracheal tube 10 and exits the cannula portion of endotracheal tube 10 near the proximal end through a suitable port or aperture 19A.

Prior art single lumen endotracheal tube 10 is typically inserted into a patient's mouth or nose, extended through the pharynx, then the larynx, and then into the trachea. Tube 10 is long enough such that the connector on proximal end 12 extends beyond the patient's mouth while the distal end 13 of tube 10 is in the trachea of the patient. After insertion of endotracheal tube 10 in the patient, the connector at proximal end 12 of endotracheal tube 10 is connected to a breathable air supply pump (not shown) and a positive pressure is maintained in the lungs by passage of the air through the connector orifice, through the lumen of endotracheal tube 10, and out the distal opening 15 of endotracheal tube 10 into the trachea of the patient. Prior to applying positive air pressure to the lungs of the patient, the doctor or medical technician will inflate cuff 17 through cuff inflation line 19 such that when the cuff is in inflated it will conform to the natural shape of trachea T while providing a seal with trachea T wall.

Figure 2A:
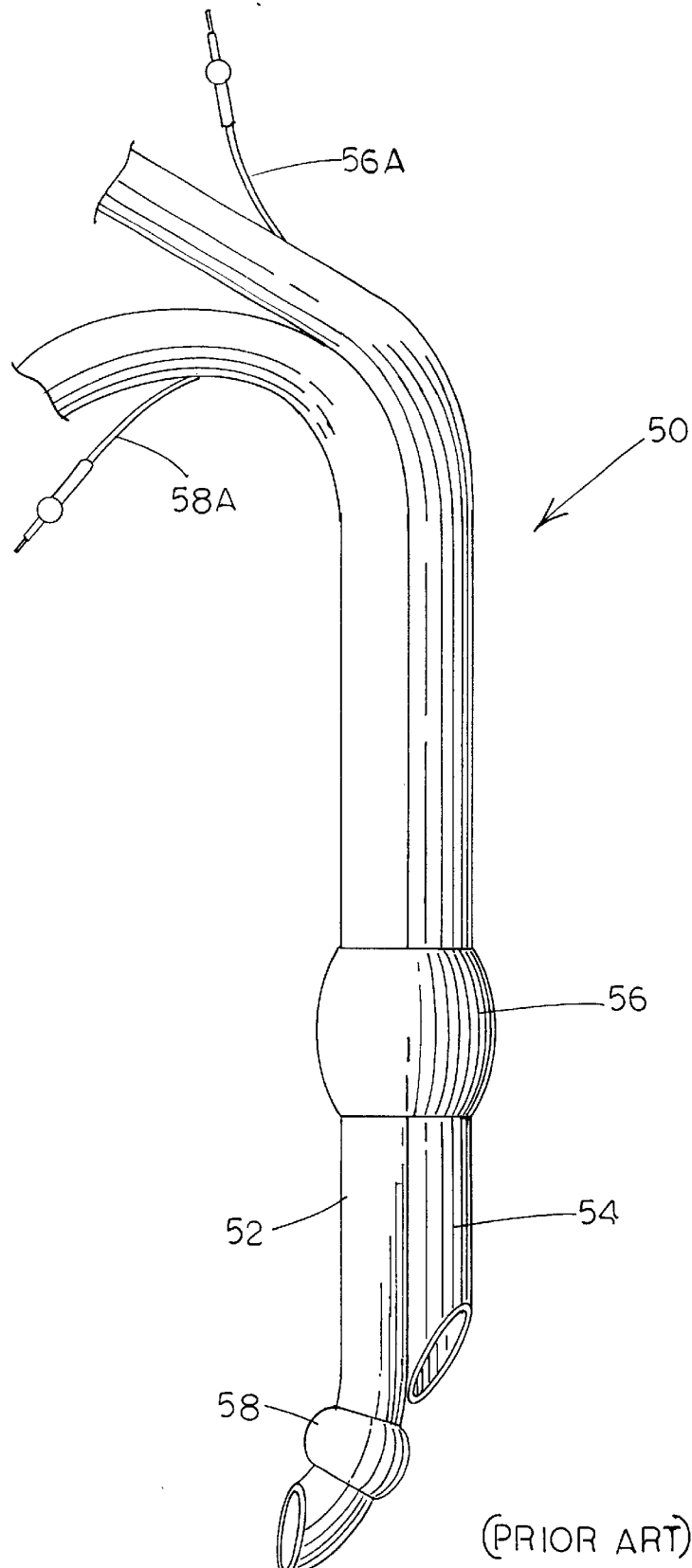
FIG. 2A is a pictorial diagram of a conventional double lumen endotracheal tube with the cuffs partially inflated.
Figure 2B:
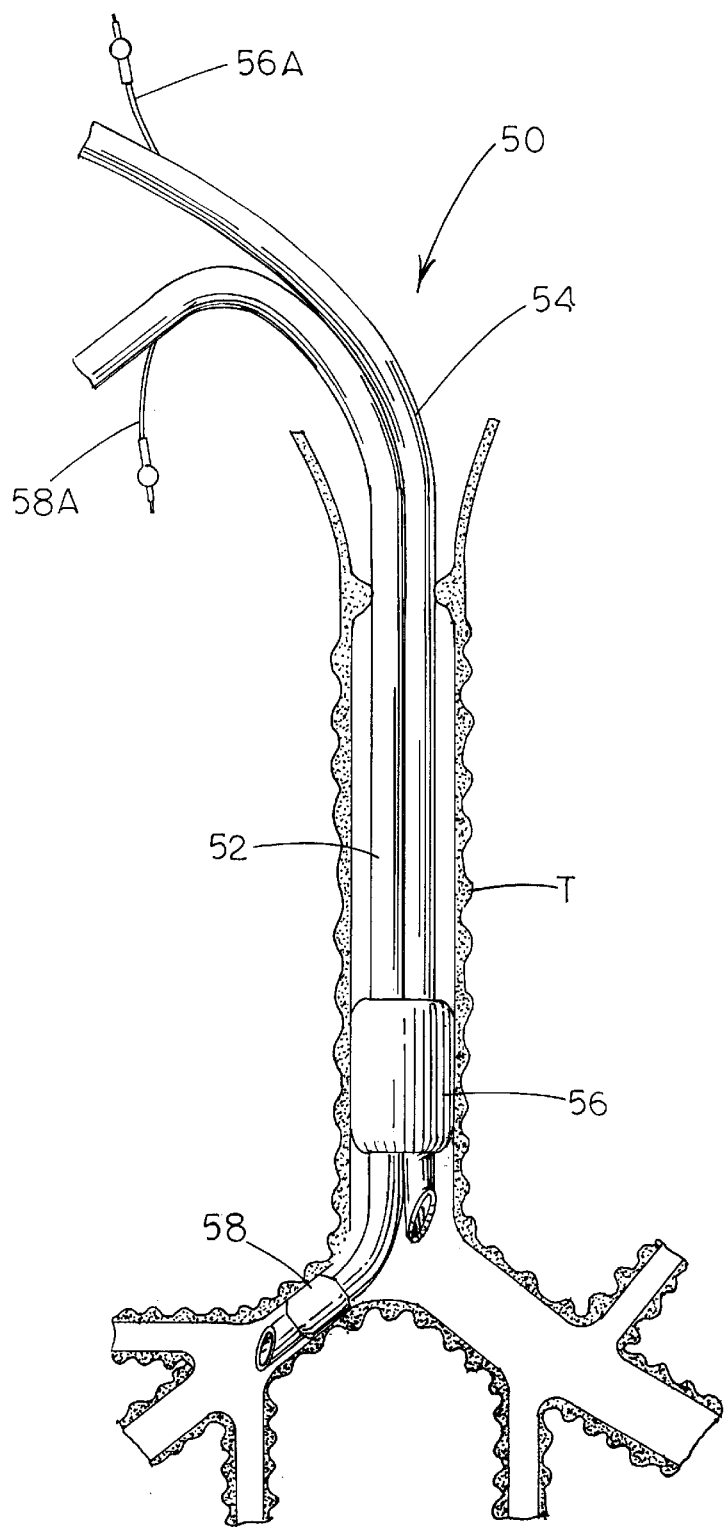
FIG. 2B is a pictorial diagram of a conventional double lumen endotracheal tube positioned in a patient with the tracheal lumen cuff inflated and the bronchial lumen cuff inflated.
Figure 5:
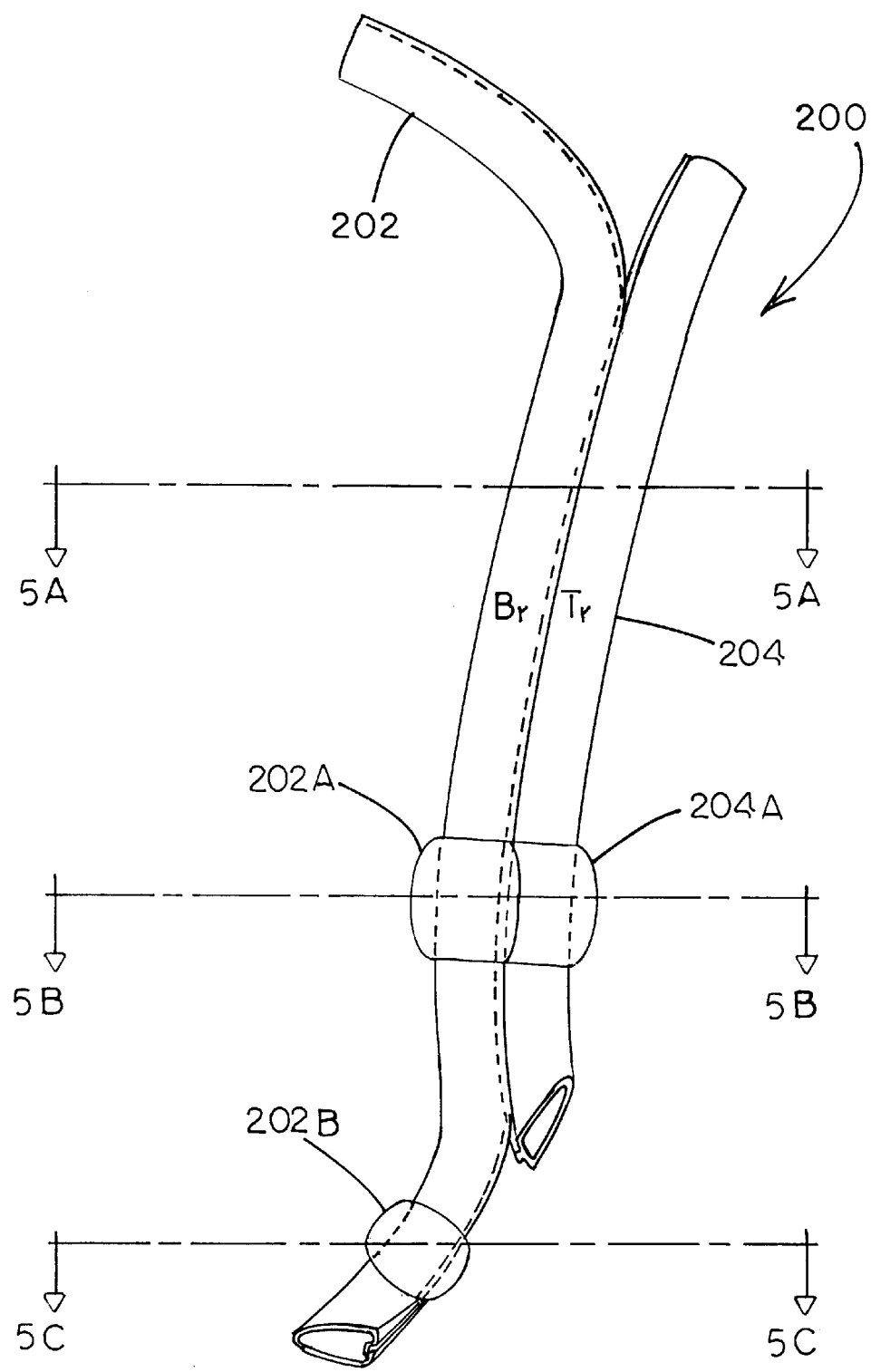
FIG. 5 is a pictorial diagram of an alternative embodiment of the separable double lumen endotracheal tube of the present invention depicting two removably affixed lumens.
Figure 6A:
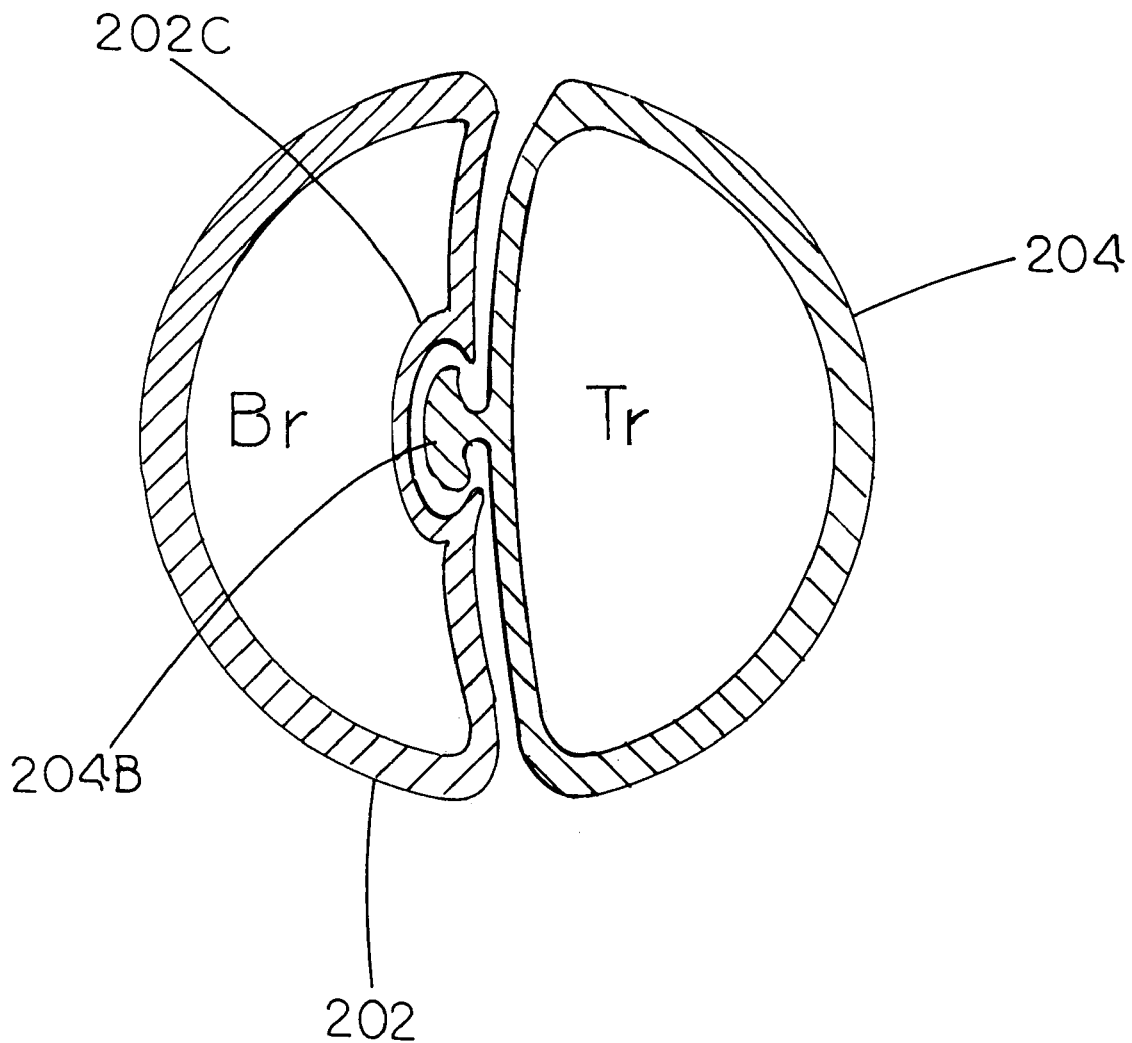
FIG. 6A is a cross-sectional view taken in the direction of arrows 5A—5A in FIG. 5.
Figure 6B:
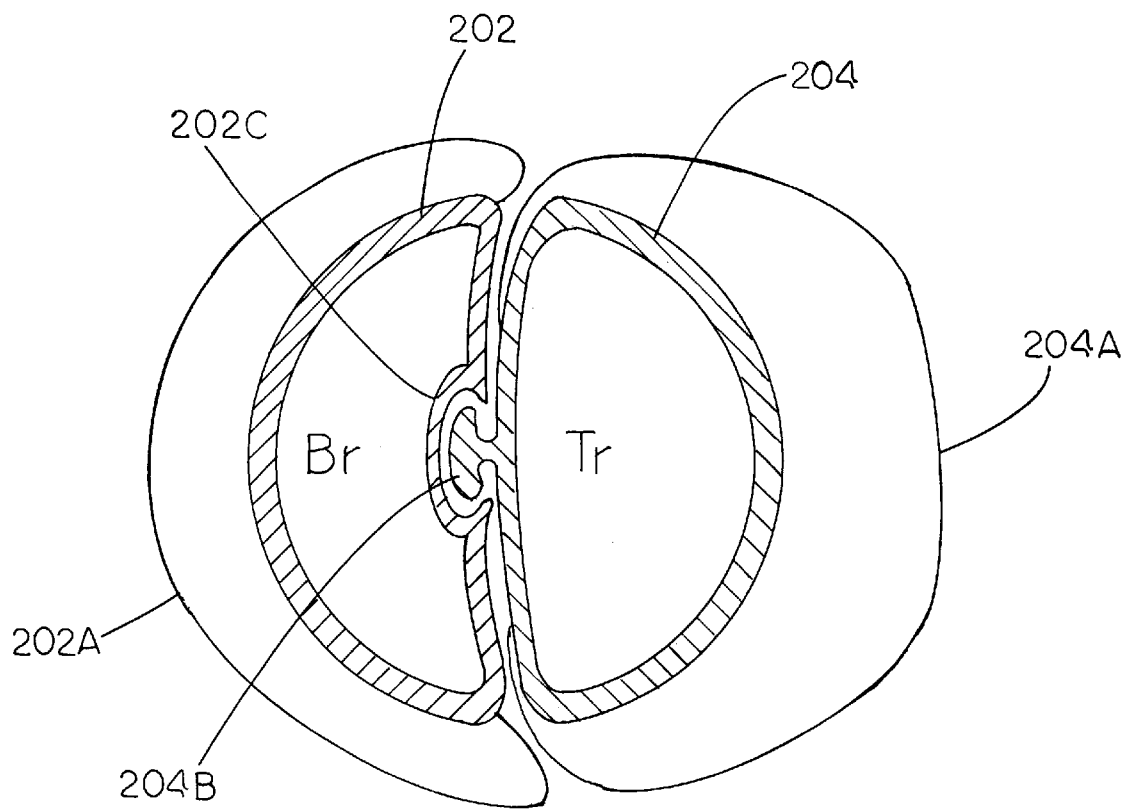
FIG. 6B is a cross-sectional view taken in the direction of arrows 5B—5B in FIG. 5.
Figure 6C:
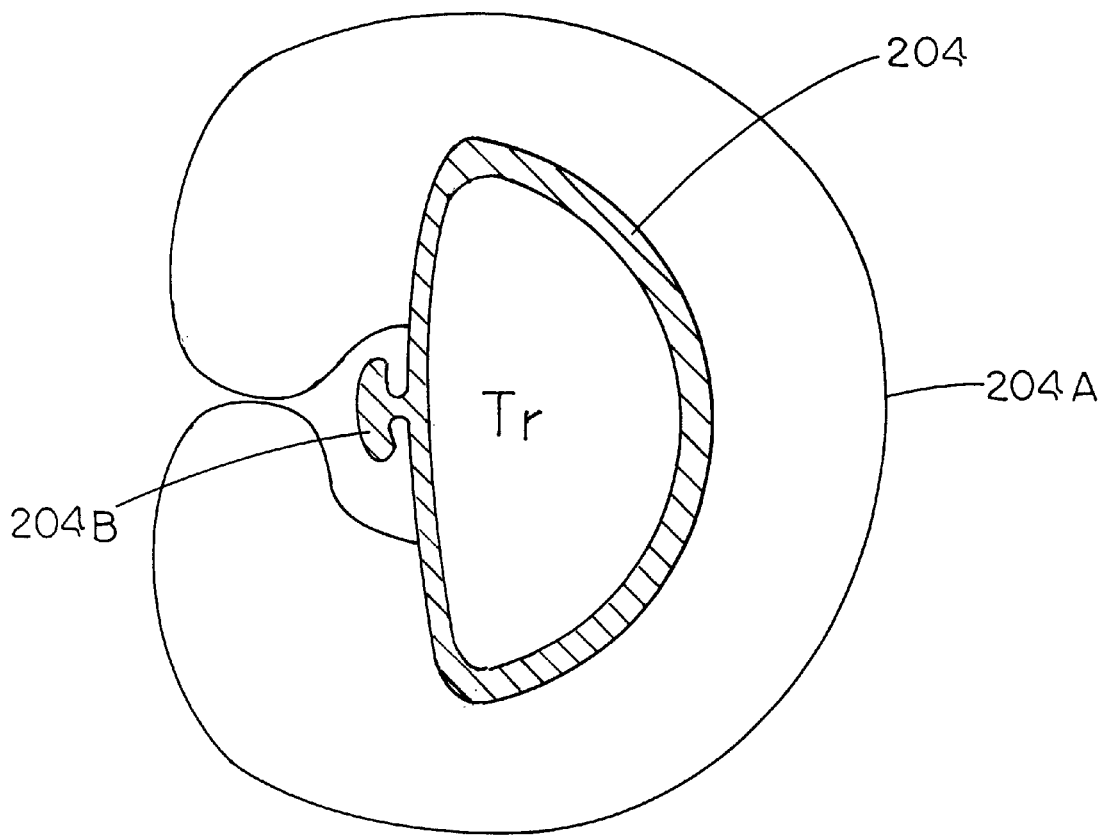
FIG. 6C is cross-sectional view similar to FIG. 6B with the bronchial lumen removed and incorporating a redundant cuff to allow apposition with the bronchial lumen removed.
Figure 6D:
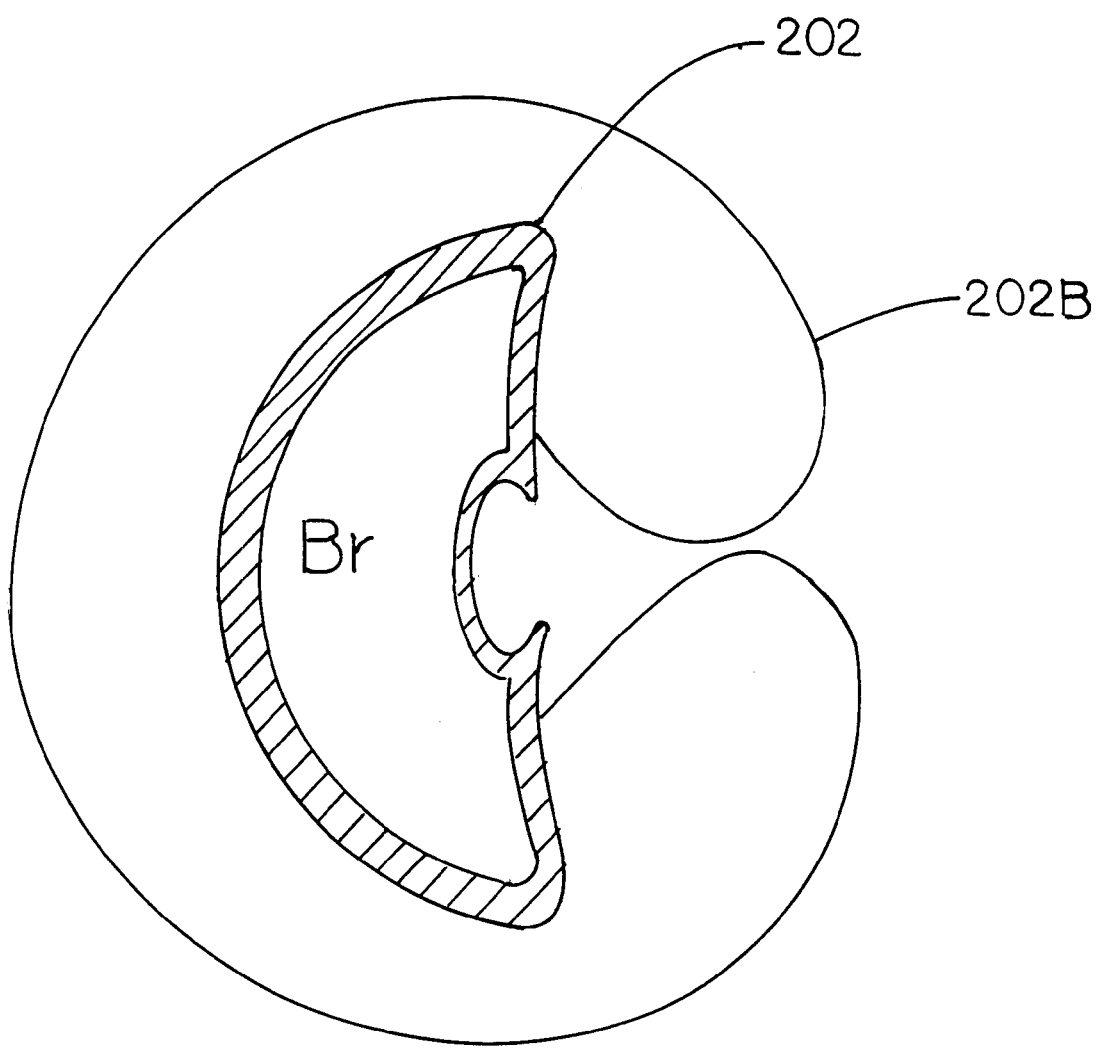
FIG. 6D is a cross-sectional view taken in the direction of arrows 5C—5C in FIG. 5 depicting a desirable bronchial cuff on the bronchial lumen which is sufficiently redundant to allow apposition.

Referring now to FIG. 2A and FIG. 2B, a prior art or conventional double lumen endotracheal tube 50 is shown. When it is necessary to ventilate both the left and right lungs separately as is the case in many kinds of lung or major vascular surgery, double lumen endotracheal tube 50 is required to be utilized. As shown in FIGS. 2A, 2B endotracheal tube 50 is a unitary structure consisting of a first lumen 52 and a second lumen 54 surrounded by inflatable cuff 56. First lumen 52 is also surrounded near its distal end by inflatable cuff 58 and cuff inflation lines 56A and 58A are provided for inflation of inflatable cuff 56 and 58, respectively. Conventional double lumen endotracheal tube 50 allows for individualized ventilation of both lungs of the patient by means of lumens 52 and 54 and cuffs 58 and 56. Lumen 52 can be extended into either the right or left mainstem bronchus (see FIG. 2B) while the remaining lumen 54 is positioned in the trachea.

The usefulness of conventional double lumen endotracheal tube 50 is limited in many circumstances by its relatively large diameter which can lead to bronchial damage and vocal cord scarring when left in place for long post-operative periods. In view of this potential problem, conventional double lumen endotracheal tube 50 is usually removed at the end of the operation and replaced with a conventional single lumen tube (see FIGS. 1A and 1B) when post-operative ventilatory support is anticipated for the patient. However, a dangerous difficulty arises when massive fluid resuscitation results in significant upper airway swelling of the patient during the course of an operation. Replacement of double lumen tube 50 with single lumen tube 10 is potentially hazardous and even life threatening since it can be difficult for the physician to see the upper airway and vocal cords sufficiently to replace single lumen endotracheal tube 10 into the patient. If the physician has difficulty replacing double lumen endotracheal tube 50 with single lumen endotracheal tube 10, the patient's life is threatened by hypoxia and asphyxiation.

In order to address this shortcoming of conventional double lumen endotracheal tube 50 and to meet the long-felt need for a safer double lumen endotracheal tube which does not pose the difficulty set forth hereinabove, the novel endotracheal tube shown in FIGS. 3A, 3B and 4A,4B was developed, The separable double lumen endotracheal tube of the present invention as shown in FIGS. 3A,3B and FIGS. 4A,4B is generally designated 100. Separable double lumen endotracheal tube 100 comprises bronchial lumen (hereinafter "bronchial tube") 102 with inflatable cuff 102A surrounding the distal end of the lumen. Tracheal lumen (hereinafter "tracheal tube") 104 is also provided, and a sheath 106 extends around both bronchial tube 102 and tracheal tube 104. Bronchial tube 102 is affixed to sheath 106 in a suitable manner such as by adhesive or co-extrusion.

Sheath 106 affixed to bronchial tube 102 is formed with perforations 106A extending lengthwise from the proximal end to the distal end thereof for the purpose which will be described in more detail hereinafter. Also, it should be appreciated that while the embodiment of separable double lumen endotracheal tube 100 shown in FIGS. 3A,3B and FIGS. 4A,4B depicts a plurality of perforations 106A extending along the length thereof for the purpose to be described in detail hereinafter, sheath 106 could also be formed with a continuous slit (not shown) extending along the length thereof which would allow the sheath to open along the length thereof when a force is applied thereto. Inflatable cuff 106B is provided around the circumference of sheath 106. In addition to bronchial tube inflatable cuff 102A and sheath inflatable cuff 106B, endotracheal tube 100 also includes an inflatable cuff 104A around tracheal tube 104 (see FIG. 4B). Cuff inflation lines 102A', 104A' and 106B' are provided for inflation of inflatable cuffs 102A, 104A and 106B, respectively.

Thus, separable double lumen endotracheal tube 100 comprises bronchial tube 102 and tracheal tube 104 which are separate plastic tubes held together by sheath 106 in contrast to the two lumens of conventional double lumen endotracheal tube 50 shown in FIGS. 2A and 2B which are extruded as a single piece of plastic. Outer sheath 106, as noted hereinbefore, is affixed to bronchial tube 102 and includes perforations 106A along the side adjacent to tracheal tube 104 in order to allow sheath 106 to open along its length in order to separate bronchial tube 102 and sheath 106 from tracheal tube 104. Thus, at the end of a surgical procedure, tracheal tube 104 can be retained in position in the patient while bronchial tube 102 and outer sheath 106 are removed from the patient by withdrawing the bronchial tube and sheath from the tracheal tube as shown in FIGS. 4A,4B of the drawings. Perforations 106A along the length of sheath 106 allow the sheath to separate when force is applied to bronchial tube 102, and bronchial tube 102 and sheath 106 can be separated and removed from a patient while retaining tracheal tube 104 in place in a patient. The inner tracheal cuff 104A will then allow positive pressure ventilation of the lungs in a standard fashion through remaining tracheal tube 104. Consequently, the complications arising from postoperative intubation with conventional double lumen endotracheal tube 50 are avoided as are the risks posed by the removal of conventional double lumen endotracheal tube 50 and replacement with conventional single lumen endotracheal tube 10.

Alternative Embodiment of Invention

FIGS. 5 and 6A–6D depict an alternative embodiment of the double lumen endotracheal tube which is generally designated 200. Double lumen endotracheal tube 200 is similar to the first embodiment of the invention 100 and comprises bronchial lumen (hereinafter "bronchial tube") 202 with inflatable tracheal cuff 202A and inflatable bronchial cuff 202B. Tracheal lumen (hereinafter "tracheal tube") 204 is provided and includes inflatable tracheal cuff 204A. Bronchial tube 202 and tracheal tube 204 are removably connectable with a tongue and groove-type connector as best seen in FIGS. 6A–6D of the drawings. The tongue and groove connector comprises a groove 202C in bronchial tube 202 which extends along a portion of the length of bronchial tube 202 and a tongue 204B which extends along a corresponding length of tracheal tube 204 and is formed so as to be slidably insertable and received within groove 202C of bronchial tube 202.

Thus, to secure bronchial tube 202 and tracheal tube 204, one needs to only insert the leading edge of tongue 204B of tracheal tube 204 into the entry of groove 202C of bronchial tube 202 and slide tracheal tube 204 downwardly relative to bronchial tube 202 until they are suitably slidably connected (or slide groove 202C of bronchial tube 202 over tongue 204B and slide bronchial tube 202 downwardly relative to tracheal tube 202). To remove bronchial tube 202 from an intubated patient, bronchial tube 202 is merely slidably removed upwardly relative to tracheal tube 204 until removal from a patient is accomplished. Thus, double lumen endotracheal tube 200 allows for the removal and reinsertion of bronchial tube 202 while the tracheal tube 204 is always present in a patient. Alternatively, but more rarely, bronchial tube 202 may remain in position and tracheal tube 204 be removed from a patient.

Summarily, separable double lumen endotracheal tube 200 allows for the detachment of bronchial tube 202 and tracheal tube 204 so that endotracheal tube 200 can function as either a tracheal tube or a bronchial tube after the lumens are separated one from the other. Further, endotracheal tube 200 allows for the removed lumen to be reinserted into a patient with the remaining tube if desired.

For example, double lumen endotracheal tube 200 allows a physician to perform the following sequence of events which are not possible with conventional endotracheal tubes:

1. Intubate trachea.
2. Intubate main stem bronchus while tracheal tube remains in place.
3. Extubate main stem bronchus while tracheal tube remains in place.

It will be understood that various details of the invention may be changed without departing from the scope of the invention. Furthermore, the foregoing description is for the purpose of illustration only, and not for the purpose of limitation—the invention being defined by the claims.

What is claimed is:

1. A separable double lumen endotracheal tube comprising:
   (a) a first tubular member comprising a length and a width defining a first ventilating lumen therethrough; and
   (b) a second tubular member comprising a length and a width defining a second ventilating lumen therethrough and being removable affixed to said first tubular lumen.

2. The separable double lumen endotracheal tube according to claim 1, wherein said first tubular member comprises a bronchial lumen and said second tubular member comprises a tracheal lumen.

3. The separable double lumen endotracheal tube according to claim 1, wherein said first tubular member and said second tubular member are removably affixed by a sheath comprising a length and a width affixed to said first tubular member and surrounding both said first and second tubular members, said sheath being formed so as to open along its length when force is applied thereto and to thereby allow said first tubular member and said sheath to be separated and removed from said second tubular member.

4. The separable double lumen endotracheal tube according to claim 3, wherein said sheath comprises perforations along the length thereof and adjacent the length of said second tubular member to allow said sheath to open and said second tubular member to be separated therefrom.

5. The separable double lumen endotracheal tube according to claim 1, wherein said first tubular member and said second tubular member are removably affixed by a tongue and groove-type connection.

6. The separable double lumen endotracheal tube according to claim 1, comprising at least one tracheal cuff.

7. The separable double lumen endotracheal tube according to claim 6, comprising a bronchial cuff.

8. A separable double lumen endotracheal tube comprising:
   (a) a first tubular member comprising a length and a width defining a bronchial ventilating lumen therethrough and comprising an outer bronchial cuff around said first tubular member;
   (b) a separately formed second tubular member comprising a length and a width defining a tracheal ventilating lumen therethrough and comprising an outer tracheal cuff around said second tubular member; and
   (c) a sheath comprising a length and a width affixed to said first tubular member so as to surround both said first and second tubular members and comprising an outer tracheal cuff around said sheath, said sheath being formed so as to open along its length when force is applied thereto and to thereby allow said first tubular member and said sheath to be separated and removed from said second tubular member.

9. The separable double lumen endotracheal tube according to claim 8, wherein said sheath comprises perforations along the length thereof and adjacent the length of said second tubular member to allow said sheath to open and said second tubular member to be separated therefrom.

10. A separable double lumen endotracheal tube comprising:
    (a) a first tubular member defining a bronchial lumen therethrough and comprising a tracheal cuff and a bronchial cuff around said first tubular member;
    (b) a separately formed second tubular member defining a tracheal lumen therethrough and comprising a tracheal cuff around said second tubular member; and
    (c) a tongue and groove-type connector serving to removably affix said first tubular member to said second tubular member and to thereby allow said first tubular member to be separated and removed from said second tubular member.

11. The separable double lumen endotracheal tube according to claim 10, wherein said tongue and groove connector comprises a longitudinal groove in said first tubular member and a mating longitudinal tongue in said second tubular member to allow said first and second tubular members to be slidably separated.

12. A method of intubating a patient with a double lumen endotracheal tube comprising:
    (a) providing a separable double lumen endotracheal tube comprising a first tubular member defining a first ventilating lumen therethrough and a removably affixed second tubular member defining a second ventilating lumen therethrough;
    (b) intubating a patient with said double lumen endotracheal tube such that said first tubular member serves as a bronchial tube and said second tubular member serves as a tracheal tube; and
    (c) removing said first or second tubular member from a patient by separating and withdrawing a tubular member from a patient such that the remaining tubular member remains in an intubated patient's airway.

13. The method according to claim 12, including inflating at least one tracheal cuff and a bronchial cuff during intubation of a patient with said double lumen endotracheal tube and deflating said at least one tracheal cuff and said bronchial cuff prior to removal of said first tubular member.

14. A separable double lumen endotracheal tube comprising:
    (a) a first tubular member comprising a length and a width defining a first lumen therethrough;
    (b) a second tubular member comprising a length and a width defining a second lumen therethrough and being removable affixed to said first tubular lumen; and
    (c) wherein said first tubular member and said second tubular member are removably affixed by a sheath comprising a length and a width affixed to said first tubular member and surrounding both said first and second tubular members, said sheath being formed so as to open along its length when force is applied thereto and to thereby allow said first tubular member and said sheath to be separated and removed from said second tubular member.

15. A separable double lumen endotracheal tube comprising:
    (a) a first tubular member comprising a length and a width defining a first lumen therethrough;
    (b) a second tubular member comprising a length and a width defining a second lumen therethrough and being removable affixed to said first tubular lumen;
    (c) wherein said first tubular member and said second tubular member are removably affixed by a sheath comprising a length and a width affixed to said first tubular member and surrounding both said first and second tubular members, said sheath being formed so as to open along its length when force is applied thereto and to thereby allow said first tubular member and said sheath to be separated and removed from said second tubular member; and
    (d) wherein said sheath comprises perforations along the length thereof and adjacent the length of said second tubular member to allow said sheath to open and said second tubular member to be separated therefrom.

16. A separable double lumen endotracheal tube comprising:
    (a) a first tubular member defining a first lumen therethrough;
    (b) a second tubular member defining a second lumen therethrough and being removable affixed to said first tubular lumen; and
    (c) wherein said first tubular member and said second tubular member are removably affixed by a tongue and groove-type connection.

17. A separable double lumen endotracheal tube comprising:
   (a) a first tubular member comprising a length and a width defining a bronchial lumen therethrough and comprising an outer bronchial cuff around said first tubular member;
   (b) a separately formed second tubular member comprising a length and a width defining a tracheal lumen therethrough and comprising an outer tracheal cuff around said second tubular member;
   (c) a sheath comprising a length and a width affixed to said first tubular member so as to surround both said first and second tubular members and comprising an outer tracheal cuff around said sheath, said sheath being formed so as to open along its length when force is applied thereto and to thereby allow said first tubular member and said sheath to be separated and removed from said second tubular member; and
   (d) wherein said sheath comprises perforations along the length thereof and adjacent the length of said second tubular member to allow said sheath to open and said second tubular member to be separated therefrom.

18. A method of intubating a patient with a double lumen endotracheal tube comprising:
   (a) providing a separable double lumen endotracheal tube comprising a first tubular member defining a first lumen therethrough and a removably affixed second tubular member defining a second lumen therethrough;
   (b) intubating a patient with said double lumen endotracheal tube such that said first tubular member serves as a bronchial tube and said second tubular member serves as a tracheal tube;
   (c) removing said first or second tubular member from a patient by separating and withdrawing said first tubular member from a patient such that the remaining tubular member remains in position in an intubated patient's trachea; and
   (d) inflating at least one tracheal cuff and a bronchial cuff during intubation of a patient with said double lumen endotracheal tube and deflating said at least one tracheal cuff and said bronchial cuff prior to removal of said first tubular member.

* * * * *